(12) United States Patent
Kozaki

(10) Patent No.: US 6,656,534 B2
(45) Date of Patent: Dec. 2, 2003

(54) MANUFACTURING METHOD FOR A GAS SENSING ELEMENT

(75) Inventor: Katsumi Kozaki, Mie-ken (JP)

(73) Assignee: Denso Corporation, Aichi-pref. (JP)

( * ) Notice: Subject to any disclaimer, the term of this patent is extended or adjusted under 35 U.S.C. 154(b) by 0 days.

(21) Appl. No.: 10/128,316

(22) Filed: Apr. 24, 2002

(65) Prior Publication Data

US 2002/0160102 A1 Oct. 31, 2002

(30) Foreign Application Priority Data

Apr. 25, 2001 (JP) ........................................ 2001-128215

(51) Int. Cl.[7] .............................. B05D 1/18; B05D 3/02; B05D 3/12
(52) U.S. Cl. ................. 427/430.1; 427/379; 427/376.1; 427/314; 427/240
(58) Field of Search ............................ 427/430.1, 379, 427/372.2, 376.1, 314, 240

(56) References Cited

U.S. PATENT DOCUMENTS 4,727,929 A * 3/1988 Simmons et al. ........... 164/516
5,593,558 A * 1/1997 Sugino et al. ............... 204/429
6,447,658 B1 * 9/2002 Wu et al. .................... 204/424
6,544,586 B1 * 4/2003 Atsumi et al. ........... 427/126.2

FOREIGN PATENT DOCUMENTS

JP          11-83789          3/1999

* cited by examiner

Primary Examiner—Michael Barr
(74) Attorney, Agent, or Firm—Nixon & Vanderhye P.C.

(57) ABSTRACT

A non-sintered element body having a predetermined shape is fabricated from powdery raw material of a solid electrolytic body. The non-sintered element body is temporarily sintered to obtain a partially-sintered element body as a semi-finished product of the solid electrolytic body. An outer surface of the partially-sintered element body is dipped into a slurry. The slurry contains surface roughing powder including large and small grains which are mutually differentiated in grain size. Then, the partially-sintered element body with a rough slurry film coated thereon is completely sintered into the solid electrolytic body.

10 Claims, 5 Drawing Sheets

MANUFACTURING METHOD FOR A GAS SENSING ELEMENT

BACKGROUND OF THE INVENTION

The present invention relates to a method for manufacturing a gas sensing element of a sensor. The gas sensor is generally installed in an exhaust gas passage of an internal combustion engine for combustion control or emission control of the internal combustion engine.

A gas sensing element is necessary to control the combustion control of an internal combustion engine. The gas sensing element has a cup-shaped solid electrolytic body having a reference gas chamber formed therein. An inside electrode is provided on an inner surface of the solid electrolytic body. An outside electrode is provided on an outer surface of the solid electrolytic body.

However, according to a conventional gas sensing element, there is the possibility that the outside electrode may separate from the solid electrolytic body.

SUMMARY OF THE INVENTION

In view of the foregoing, the present invention has an object to provide a method for manufacturing a gas sensing element having an excellent bonding strength between an outside electrode and a solid electrolytic body.

In order to accomplish the above and other related objects, the present invention provides a method for manufacturing a gas sensing element which has a cup-shaped solid electrolytic body having a reference gas chamber formed therein, an inside electrode provided on an inner surface of the solid electrolytic body, and an outside electrode provided on an outer surface of the solid electrolytic body. The manufacturing method of this invention comprises a step of forming a non-sintered element body having a predetermined shape from powdery raw material of the solid electrolytic body, a step of temporarily sintering the non-sintered element body to obtain a partially-sintered element body as a semi-finished product of the solid electrolytic body, a step of dipping an outer surface of the partially-sintered element body into a slurry containing surface-roughing powder including large and small grains which are mutually differentiated in grain size, and a step of completely sintering the partially-sintered element body with a rough slurry film coated thereon into the solid electrolytic body.

According to this invention, the outer surface of the partially-sintered element body is dipped into the slurry containing the surface-roughing powder including large and small grains. The slurry film with the mixed large and small grains is formed on the outer surface of the partially-sintered element body. Then, the complete sintering treatment is performed. Accordingly, the outer surface of the completely sintered solid electrolytic body is finished into a rough surface whose roughness depends on the grain size and the mixing ratio of the large and small grains.

The outside electrode is fixed to the outer surface of the sintered solid electrolytic body, after the outer surface is finished into the rough surface. The rough surface brings anchor effect. In other words, the rough surface assures an excellent bonding strength required for firmly fixing other member thereon. Thus, according to the manufacturing method of the present invention, the outside electrode can be firmly fixed on the outer surface of the solid electrolytic body due to the anchor effect brought by the coated rough surface. In other words, this invention provides an excellent method for manufacturing a gas sensor which is capable of effectively preventing the outside electrode from peeling off the solid electrolytic body and is also capable of assuring excellent durability.

According to the manufacturing method of the present invention, the surface roughness of the solid electrolytic body can be easily changed or adjusted by adequately selecting the grain size of the large and small grains and their contents relative to the slurry. Thus, the manufacturing method of this invention is easily realized and brings the effect of cost reduction.

As understood from the foregoing, according to the present invention, it becomes possible to obtain a manufacturing method of a gas sensor which assures an excellent bonding force for the outside electrode bonded on the outer surface of the solid electrolytic body.

According to the present invention, for the purpose of preventing the outside electrode from being directly exposed to the measured gas, it is preferable to provide a trap layer and/or a protective layer so as to cover the outside electrode. The trap layer traps poisonous or harmful substances contained in the measured gas.

Furthermore, it is also preferable to provide a diffusion resistive layer so as to cover the outside electrode. The diffusion resistive layer controls the time required for the measured gas to reach the outside electrode. The diffusion resistive layer further controls the amount of the measured gas reaching the outside electrode.

In this case, according to the manufacturing method of the present invention, the outer surface of the solid electrolytic body is finished into a rough surface. The rough surface brings a strong bonding force required for firmly fixing the outside electrode on the outer surface of the solid electrolytic body. The rough surface also brings a sufficient bonding force required for firmly fixing the additional layers on the outside electrode. The additional layers provided on the outside electrode include the trap layer, the protective layer, and the diffusion resistive layer.

Accordingly, the present invention makes it possible to prevent the outside electrode from peeling off the outer surface of the solid electrolytic body. Furthermore, the present invention makes it possible to prevent each additional layer from peeling off the outside electrode or the outer surface of the solid electrolytic body.

Furthermore, the portion of the solid electrolytic body to be dipped into the slurry containing the surface roughing powder can be limited to a specific region where the outside electrode is provided.

It is preferable that a coating area of the rough surface is sufficiently wide to entirely cover the region where the outside electrode is provided. However, the effect of the present invention can be obtained even when the coating area of the rough surface is somewhat smaller than the entire area of the outside electrode.

Furthermore, when the trap layer, the protective layer, and the diffusion resistive layer are provided on the outside electrode or on the outer surface of the solid electrolytic body, it is preferable to dip the corresponding portion of the solid electrolytic body into the slurry containing the surface roughing powder.

With this arrangement, it becomes possible to assure a strong bonding force required for firmly fixing these additional layers together with the outside electrode on the outer surface of the solid electrolytic body.

Furthermore, the gas sensing element is generally equipped with electric leads and terminals connected to the inside and outside electrodes for outputting a sensing signal from the electrodes or applying a voltage to the electrodes. Thus, some of the leads and terminals are provided on the outer surface of the solid electrolytic body.

In this case, to increase the bonding strength for fixing the leads and terminals on the outer surface of the solid electrolytic body, it is preferable to dip the portion of the solid electrolytic body corresponding to the leads and the terminals into the slurry containing the surface roughing powder.

Furthermore, it is preferable that the material of the surface roughing powder is identical with that of the solid electrolytic body. It is also preferable that the surface roughing powder can be integrated with the solid electrolytic body through the sintering treatment.

This is effective to prevent the slurry film containing the surface roughing powder from peeling off the solid electrolytic body.

Furthermore, a binder is generally added with the grains to form the slurry containing the surface roughing powder. A preferable binder is PVA (polyvinyl alcohol).

According to the manufacturing method of this invention, it is preferable that a coating density of the slurry during the step of dipping the outer surface of the partially-sintered element body is in a range of 0.05 mg/mm$^2$ to 0.30 mg/mm$^2$ in terms of the amount of the surface-roughing powder contained in the slurry.

Setting the coating density to a value in the above-described preferable range is effective to prevent the outside electrode from peeling off the outer surface of the solid electrolytic body. Furthermore, it is effective to enhance the bonding strength of the protective layer.

If the coating density is less than 0.05 mg/mm$^2$, it will be difficult to obtain a sufficient bonding force for fixing the outside electrode and the protective layer on the solid electrolytic body. On the other hand, if the coating density is larger than 0.30 mg/mm$^2$, the strength of the coated rough surface will be worsened.

Furthermore, according to the manufacturing method of this invention, it is preferable that the grain size of the large grains is in a range from 5 $\mu$m to 50 $\mu$m.

In this case, it becomes possible to form a preferable outside electrode. It becomes possible to assure a strong bonding force required for fixing the outside electrode and the protective layer on the solid electrolytic body.

If the grain size of the large grains is less than 5 $\mu$m, it will be difficult to form the rough surface having a sufficient surface roughness required for preventing the outside electrode from peeling off the solid electrolytic body. On the other hand, if the grain size of the large grains is larger than 50 $\mu$m, it will be difficult to form an appropriate outside electrode.

Furthermore, according to the manufacturing method of this invention, it is preferable that the grain size of the small grains is not larger than 1 $\mu$m.

This is effective to assure an appropriate holding force for holding the large grains. If the grain size of the small grains is larger than 1 $\mu$m, it will be difficult to obtain a sufficient holding force for holding the large grains.

Furthermore, according to the manufacturing method of this invention, it is preferable that the grain size of the small grains is in a range from 0.1 $\mu$m to 1 $\mu$m.

This is effective to assure an appropriate holding force for holding the large grains. If the grain size of the small grains is less than 0.1 $\mu$m, it will encounter the problem in handling the powder, such as flying off of micro powder. On the other hand, if the grain size of the small grains is larger than 1 $\mu$m, it will be difficult to obtain a sufficient holding force for holding the large grains.

Furthermore, according to the manufacturing method of this invention, it is preferable that the entire content of the large grains is in a range from 5 weight % to 20 weight % when the slurry is 100 weight %.

This is effective to obtain an adequate bonding force required for fixing the outside electrode and the protective layer on the solid electrolytic body.

If the entire content of the large grains is less than 5 weight %, it will be difficult to obtain a sufficient bonding force required for fixing the outside electrode and the protective layer on the solid electrolytic body. On the other hand, if the entire content of the large grains is larger than 20 weight %, the large grains may fall off the slurry film.

Furthermore, according to the manufacturing method of this invention, it is preferable that the entire content of the small grains is in a range from 10 weight % to 20 weight % when the slurry is 100 weight %.

This is effective to assure an adequate holding force required for holding the large grains. If the entire content of the small grains is less than 10 weight %, the large grains may fall off the slurry film. On the other hand, if the entire content of the large grains is larger than 20 weight %, it will be difficult to assure a sufficient bonding force required for fixing the outside electrode and the protective layer on the solid electrolytic body.

According to the manufacturing method of the present invention, it is preferable that the step of dipping the outer surface of the partially-sintered element body into the slurry containing the surface-roughing powder is performed in such a manner that a slurry film is formed on the outer surface of the partially-sintered element body, the large grains protrude from a surface level of the slurry film and are spaced from each other, and the following relationship is satisfied, $$0.25d \leq t \leq 0.75d$$

wherein 'd' represents a grain diameter of the large grains and 't' represents a thickness of the slurry film.

Dipping the partially-sintered element body into the slurry results in formation of the slurry film on the outer surface of the partially-sintered element body. Satisfying the above-described relationship between the grain diameter of the large grains and the film thickness leads to formation of an excellent slurry film having a sufficient surface roughness.

More specifically, due to size difference between the large grains and the smaller grains, the large grains protrude from the surface level of the slurry film as later explained with reference to FIG. 1A. In this case, the surface roughness of the slurry film can be expressed by a difference between the grain size of large grains and the slurry film thickness. The small grains are completely embedded in the slurry film.

If the slurry film thickness 't' is less than 0.25d, the large grains may fall off the slurry film. On the other hand, if the slurry film thickness 't' is larger than 0.75d, it will be difficult to assure a sufficient bonding force for firmly fixing the outside electrode and the protective layer on the solid electrolytic body.

Furthermore, it is preferable that the manufacturing method of the present invention further comprises the following steps for dipping the outer surface of the partially-sintered element body into the slurry containing the surface-roughing powder:

a step of preparing a slurry tank equipped with a stirrer therein;

a step of rotating the stirrer to cause rotational flow of the slurry in the slurry tank;

a step of dipping the partially-sintered element body in the slurry in a condition where the stirrer is rotating or stopped; and a step of lifting the partially-sintered element body out of the slurry tank.

This is effective to prevent the surface roughing powder from sedimenting in the slurry. The slurry concentration will be kept uniformly. This assures that the surface roughing powder is adequately attached on the outside surface of the partially-sintered element body.

It is preferable that a plurality of partially-sintered element bodies are hung on a common jig so that the plurality of partially-sintered element bodies can be dipped into the slurry at a time.

It is also possible to hang each partially-sintered element body on an independent jig.

Moreover, a stirrer or a rotary vane is preferably used to stir the slurry.

Furthermore, it is preferable that the manufacturing method of the present invention further comprises the following steps for dipping the outer surface of the partially-sintered element body into the slurry containing the surface-roughing powder:

a step of preparing a slurry tank filled with the slurry;

a step of rotating the partially-sintered element body about its center axis and dipping the partially-sintered element body into the slurry when a stirrer is rotated in the slurry tank, or dipping the partially-sintered element body into the slurry without rotating the partially-sintered element body when the stirrer is not rotated in the slurry tank; and a step of lifting the partially-sintered element body out of the slurry tank.

In this case, the slurry is adequately stirred. The partially-sintered element body is rotated and dipped into the slurry when rotational flow of the slurry is kept. The partially-sintered element body is not rotated and dipped into the slurry when rotational flow of the slurry substantially disappears. In other words, the dipping treatment of this invention is performed in such a manner that no relative rotation is caused between the partially-sintered element body and the slurry tank.

Thus, the dipping treatment of this invention assures uniform coating of the slurry film containing the surface roughing powder on the outside surface of the partially-sintered element body.

BRIEF DESCRIPTION OF THE DRAWINGS

The above and other objects, features and advantages of the present invention will become more apparent from the following detailed description which is to be read in conjunction with the accompanying drawings, in which.

DESCRIPTION OF THE PREFERRED EMBODIMENTS

Figure 1A:
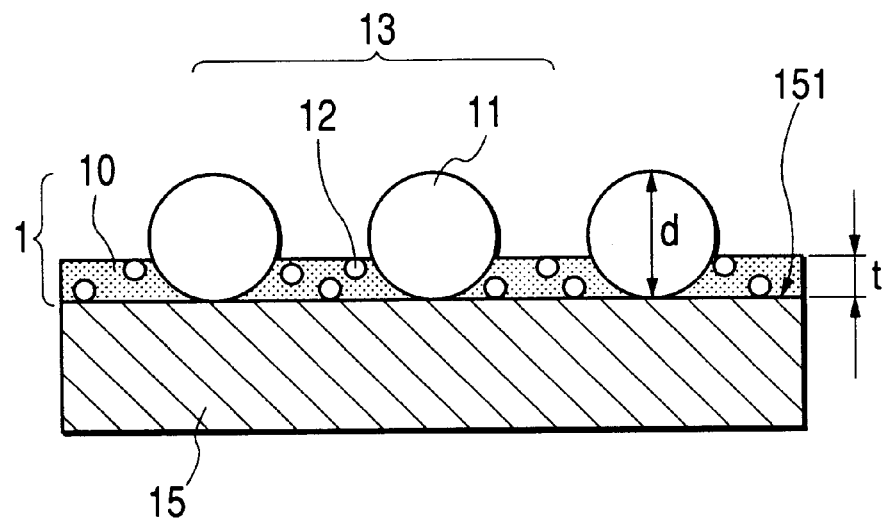
FIG. 1A is a cross-sectional view showing a slurry film formed on a partially-sintered element body in accordance with a first embodiment of the present invention.

Preferred embodiments of the present invention will be explained hereinafter with reference to attached drawings. Identical parts are denoted by the same reference numerals throughout the drawings.

First Embodiment

Hereinafter, a gas sensor manufacturing method according to a preferred embodiment of the present invention will be explained.

Figure 2:
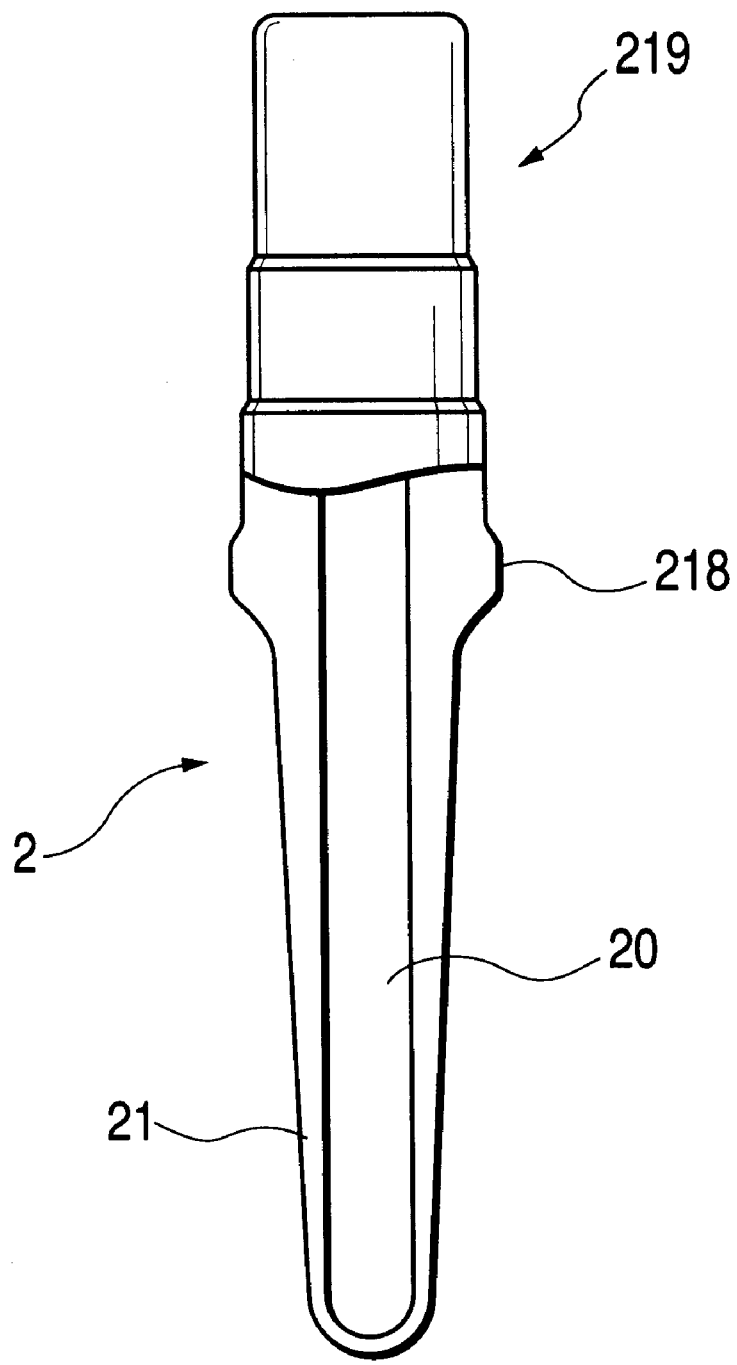
FIG. 2 is a partly cross-sectional view showing a gas sensing element to which the surface roughing treatment is applied in accordance with the first embodiment of the present invention.
Figure 3:
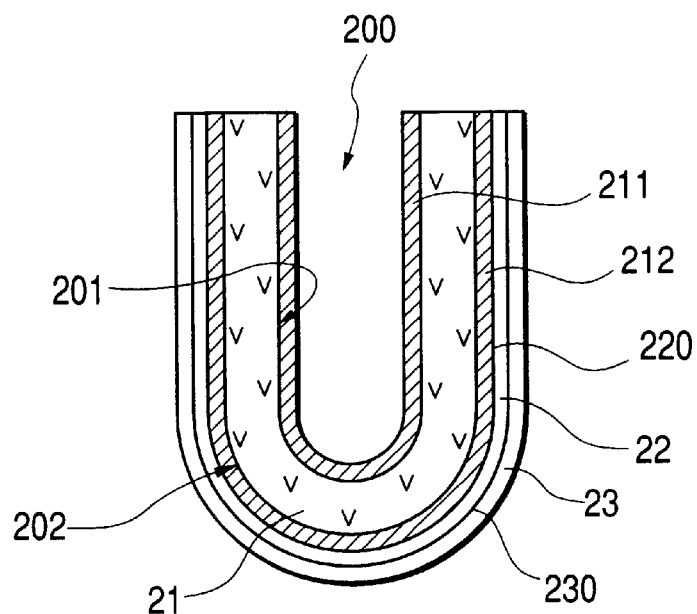
FIG. 3 is a cross-sectional view showing a detailed arrangement of the gas sensing element to which the surface roughing treatment is applied in accordance with the first embodiment of the present invention.

FIGS. 2 and 3 show a gas sensing element 2 of a gas sensor in accordance with a first embodiment of the present invention. The gas sensing element 2 has a cup-shaped solid electrolytic body 21 with a reference gas chamber 20 defined therein. An inside electrode 211 is provided on an inner surface 201 of solid electrolytic body 21. An outside electrode 212 is provided on an outer surface 202 of solid electrolytic body 21.

The solid electrolytic body 21 of gas sensing element 2 is manufactured in the following manner.

First, a non-sintered element body having a predetermined shape (i.e., cup-shaped configuration) is formed from powdery raw material of the solid electrolytic body 21. The non-sintered element body is temporarily sintered to obtain a partially-sintered element body 15 as a semi-finished product of the solid electrolytic body 21.

Next, an outer surface 151 of the partially-sintered element body 15 is dipped into a slurry. The slurry contains surface roughing powder 13 consisting of large grains 11 and small grains 12 which are mutually differentiated in grain size. The grain diameter of large grains 11 is larger than the grain diameter of small grains 12. Then, the partially-sintered element body 15 is completely sintered into the solid electrolytic body 21.

Hereinafter, the manufacturing method of this embodiment will be explained in more detail.

The gas sensing element 2 of this embodiment is attached to an exhaust gas passage of an automotive engine. The gas sensing element 2 is employed to detect the oxygen concentration in the exhaust gas to control an air-fuel ratio of an automotive engine. In other words, the gas sensing element 2 functions as part of the fuel combustion control system or the exhaust gas purification system.

The gas sensing element 2, as shown in FIGS. 2 and 3, comprises the cup-shaped solid electrolytic body 21 made of an oxygen ion conductive zirconia, the inside electrode 211 provided on the inner surface 201 of solid electrolytic body 21, and the outside electrode 212 provided on the outer surface 202 of solid electrolytic body 21. The inside electrode 211 provided on the inner surface 201 of solid electrolytic body 21 is exposed to a reference gas (e.g., air) filled in the reference gas chamber 20 defined in the solid electrolytic body 21. The outside electrode 212 provided on the outer surface 202 of solid electrolytic body 21 is exposed to the exhaust gas of the automotive engine.

Although not shown in the drawing, to detect an output of the gas sensing element 2, leads and terminals of gas sensing element 2 are provided on the inner and outer surfaces 201 and 202 of solid electrolytic body 21.

The inside electrode 211 and the outside electrode 212 are platinum electrodes.

An alumina ceramic spray coating layer 22 is provided on a surface 220 of outside electrode 212. The spray coating layer 22 is formed by plasma spraying. The spray coating layer 22 has slight gas permeability. A porous layer 23 covers a surface 230 of the spray coating layer 22. The porous layer 23 functionally serves as a trap layer for trapping poisonous or harmful substances contained in the exhaust gas (i.e., the objective gas to be measured). The spray coating layer 22 functionally serves as a diffusion resistive layer which controls the time required for the exhaust gas to reach the outside electrode 212. The spray coating layer 22 (i.e., the diffusion resistive layer) also controls the amount of the exhaust gas reaching the outside electrode 212.

Next, the method for manufacturing the gas sensing element 2 of this invention will be explained.

First, the powdery raw material of solid electrolytic body 21 is prepared. The powdery raw material of solid electrolytic body 21 comprises zirconia and yttria. The powdery raw material of solid electrolytic body 21 is ground into granulated powder having a predetermined grain size.

The granulated powder is then formed into the non-sintered element body and is temporarily sintered to obtain a partially-sintered element body having a predetermined shape.

Furthermore, a part of the granulated powder is utilized to form the surface roughing powder 13.

More specifically, the granulated powder is temporarily sintered. A part of the granulated powder is directly utilized as the large grains 11. The rest of the granulated powder is further granulated into the small grains 12.

The large grains 11 and the small grains 12 thus obtained are mixed with water and binder to obtain a slurry.

The surface roughing powder 13 contained in the slurry of this embodiment consists of large grains having an average grain diameter of 40 μm and small grains having an average grain diameter of 0.8 μm. The mixing ratio of the large grains to the small grains is 50:50 in weight.

Figure 4:
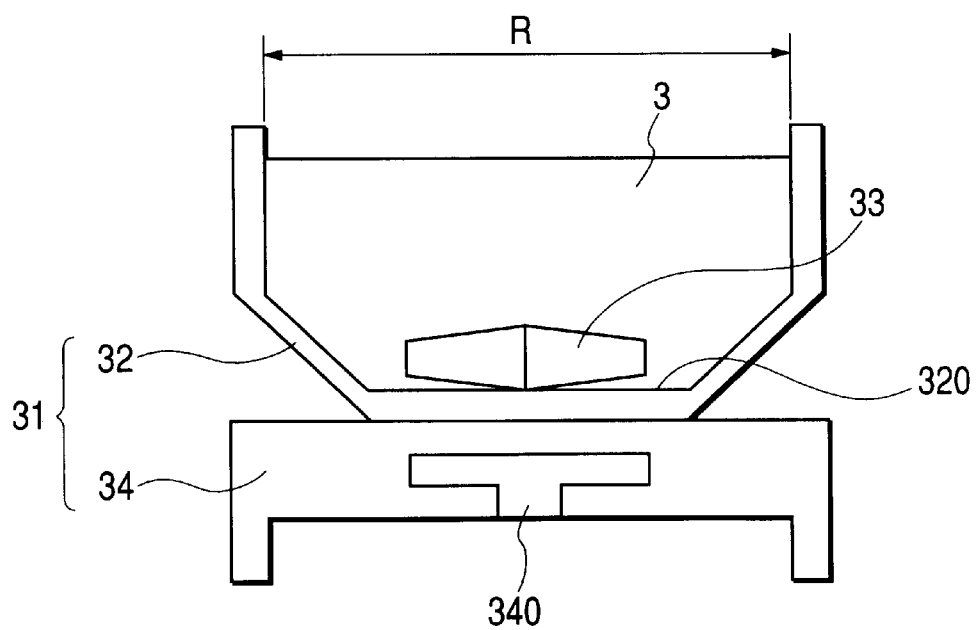
FIG. 4 is a schematic view explaining a slurry tank in accordance with the first embodiment of the present invention.

The slurry is put into a slurry tank 31 as shown in FIG. 4. The slurry tank 31 comprises a slurry container 32 mounted on a motor base 34. The motor base 34 has a built-in motor (not shown) equipped with a magnet 340. An inner diameter R of slurry container 32 is 180 mm. A stirrer 33 is provided on a bottom 320 of the slurry container 32. The stirrer 33 is equipped with a magnet (not shown). The magnet of stirrer 33 and the magnet 340 of motor base 34 attract each other. Accordingly, the stirrer 33 rotates in accordance with rotation of the motor.

Figure 5:
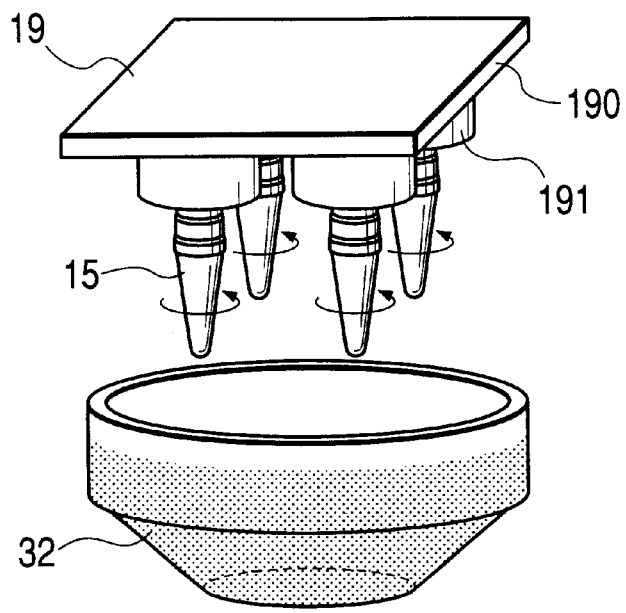
FIG. 5 is a perspective view showing a surface roughing treatment using a common slurry tank for simultaneously dipping four partially-sintered element bodies in accordance with the first embodiment of the present invention.

Next, as shown in FIG. 5, a total of four partially-sintered element bodies 15 are hung on a jig 19. The jig 19 comprises a base plate 190 and four attachments 191. Each attachment 191 independently hangs a single partially-sintered element body 15. The partially-sintered element body 15 is rotatably supported by the attachment 191. The partially-sintered element body 15 rotates about its center axis. The attachment 191 covers a portion of the partially-sintered element body 15 which corresponds to a base portion 219 of solid electrolytic body 21. The jig 19 is positioned above the slurry container 32.

Next, the motor is driven. The magnet 340 of motor base 34 rotates. The magnet 340 of motor base 34 magnetically attracts the magnet of stirrer 33. The stirrer 33 rotates in accordance with rotation of the motor because of magnetic coupling between the magnet 340 of motor base 34 and the magnet of stirrer 33. The jig 19 is lowered to dip the partially-sintered element body 15 into the slurry 3 stored in the slurry container 32 while the stirrer 33 is kept rotating. The partially-sintered element body 15 is rotated about its center axis in the slurry 3. For example, the rotational speed of stirrer 33 is set to 230 rpm. The rotational speed of partially-sintered element body 15 is set to 160 rpm.

After a predetermined time has passed, the jig 19 is raised upward to get the partially-sintered element body 15 out of the slurry 3.

Figure 1B:
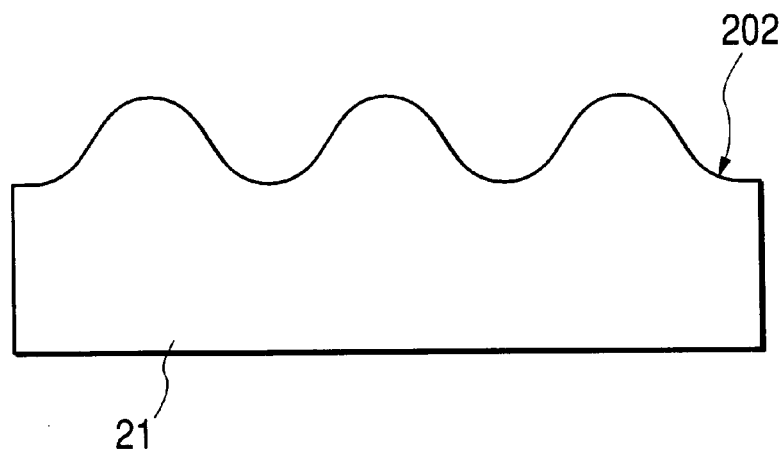
FIG. 1B is a view explaining the surface roughing treatment applied to the outer surface of the solid electrolytic body in accordance with the first embodiment of the present invention.

FIG. 1A shows a slurry film 1 formed on the partially-sintered element body 15 through the above-described processes. Then, the partially-sintered element body 15 is completely sintered to obtain the solid electrolytic body 21 whose outer surface 202 is finished into a rough surface as shown in FIG. 1B.

The slurry film 1 extends from a distal end (i.e., closed end of solid electrolytic body 21) to the vicinity of a barrel portion 218 of the solid electrolytic body 21. The barrel portion 218 protrudes radially outward. The solid electrolytic body 21 has a maximum outer diameter at the barrel portion 218.

As shown in FIG. 1A, the thickness 't' of slurry film 1 represents a coating layer 10 consisting of the binder and small grains 12. According to this embodiment, the thickness 't' of the coating layer 10 is 0.025 mm. The grain diameter 'd' of large grains 11 is 0.040 mm. The thickness 't' of the coating layer 10 is approximately half of the grain diameter 'd' of large grains 11.

The inside electrode 211 and the outside electrode 212 are provided on the inner and outer surfaces of solid electrolytic body 21. The spray coating layer 22, which is a dense alumina layer, is coated on the outside electrode 212 by plasma spray. The spray coating layer 22 covers the entire surface of outside electrode 212. A porous alumina layer is provided on the spray coating layer 22. The porous alumina layer covers the entire surface of outside electrode 212. The porous alumina layer is formed into a porous layer 23 through dipping and sintering treatments.

Thus, the gas sensing element 2 of this embodiment is obtained.

This embodiment of the present invention brings the following functions and effects.

According to this embodiment, as shown in FIG. 1A, the slurry film 1 containing the large grains 11 and small grains 12 is coated on the outer surface of partially-sintered element body 15. The partially-sintered element body 15 is then completely sintered to obtain the solid electrolytic body 21.

Accordingly, as shown in FIG. 1B, the outer surface 202 of solid electrolytic body 21 is finished into the rough surface whose roughness depends on the grain size and the mixing ratio of the large and small grains 11 and 12.

The outside electrode 212 is fixed on such a rough surface. The rough surface brings anchor effect which assures an excellent bonding strength. The outside electrode 212 is firmly fixed to the outer surface 202 of solid electrolytic body 21 due to the anchor effect brought by the rough surface. Thus, it becomes possible to obtain the gas sensing element 2 which is capable of effectively preventing the outside electrode 212 from peeling off the solid electrolytic body 21 and is also capable of assuring excellent durability.

Furthermore, the anchor effect brought by the rough surface of this embodiment is applicable to the fixing or bonding of the leads and the terminals (not shown) provided together with the outside electrode 212 as well as to the fixing or bonding of the spray coating layer 22 and the porous layer 23 covering the outside electrode 212.

According to the embodiment of this invention, the surface roughness of the solid electrolytic body 21 can be easily changed or adjusted by adequately selecting the grain size of large grains 11 and small grains 12 and their contents relative to the slurry 3. Thus, the manufacturing method of this embodiment is easily realized and is non-expensive in the cost.

As described above, the first embodiment brings an excellent method for manufacturing a gas sensor which assures an excellent bonding force for the outside electrode bonded on the outer surface of the solid electrolytic body.

Figure 6:
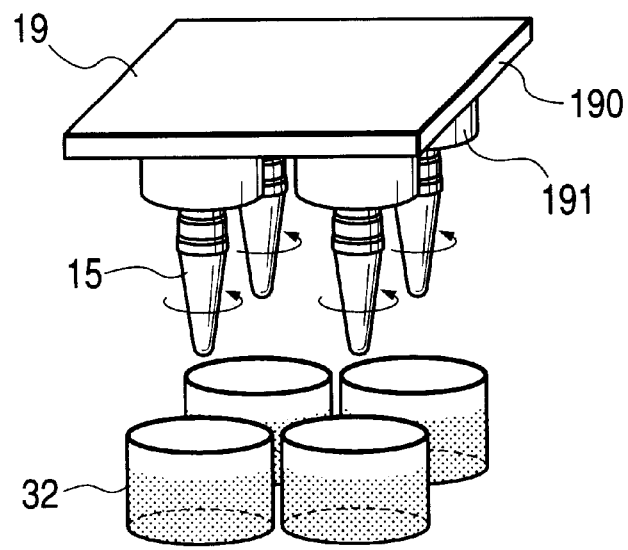
FIG. 6 is a perspective view showing a surface roughing treatment using separate slurry tanks each dipping a single partially-sintered element body in accordance with the first embodiment of the present invention.

According to the above-described embodiment, a total of four partially-sintered element bodies 15 are simultaneously dipped into the slurry 3 stored in the common slurry tank 31. However, as shown in FIG. 6, it is possible to prepare an independent slurry container 32 for each partially-sintered element body 15. Although not shown, each slurry container 32 is equipped with an independent stirrer 33.

Second Embodiment

A second embodiment of this invention relates to a method for simultaneously forming the slurry films of numerous partially-sintered element bodies.

Figure 7:
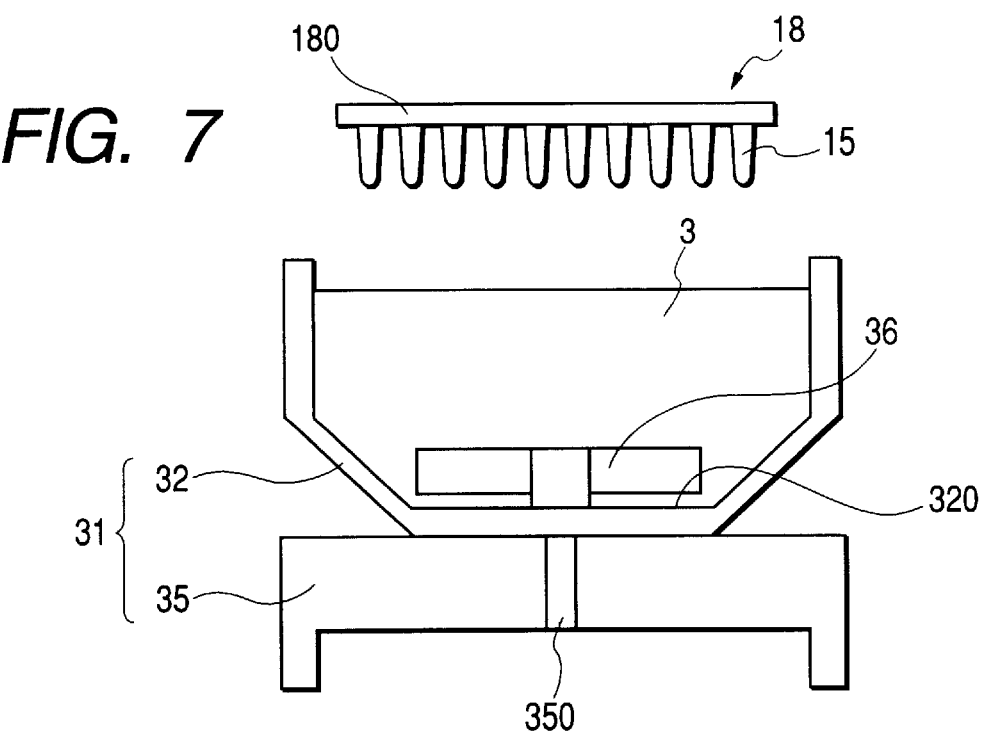
FIG. 7 is a schematic view showing a surface roughing treatment using a common slurry tank for simultaneously dipping a plurality of partially-sintered element bodies in accordance with a second embodiment of the present invention.

As shown in FIG. 7, a slurry tank 31 of the second embodiment is fixed to a motor shaft 350 of a motor. A rotary vane 36 with four blades is provided on the bottom 320 of the slurry container 32. The rotary vane 36 is rotatable together with the motor shaft 350. An inner diameter of slurry container 32 is 320 mm. The rotary vane 36 is functionally equivalent to the stirrer 33. The motor shaft 350 is accommodated in a motor base 35.

In response to rotation of the motor, the rotary vane 36 rotates about its axis and stirs the slurry 3 stored in the slurry container 32.

The dipping treatment using the slurry tank 31 of the second embodiment is performed in the following manner.

The slurry 3 of the second embodiment is identical with that of the first embodiment. The slurry 3 of the second embodiment is fabricated from the surface roughing powder consisting of large and small grains. The surface roughing powder 13 contained in the slurry 3 of second embodiment consists of large grains having an average grain diameter of 40 $\mu$m and small grains having an average grain diameter of 0.8 $\mu$m. However, according to the second embodiment, the mixing ratio of the large grains to the small grains is set to 35:65 in weight.

A jig 18 of the second embodiment comprises a base plate 180. A total of 95 attachments (not shown), each hanging a partially-sintered element body 15, are provided on a lower surface of the base plate 180. The jig 18 is positioned above the slurry container tank 31.

Next, the motor is driven to rotate the rotary vane 36. The slurry 3 is stirred by the rotary vane 36. The rotational speed of the motor (i.e., the rotary vane 36) is 200 rpm. Then, the rotation of rotary vane 36 is once stopped to wait the flow of slurry 3 is stabilized to a certain degree.

Next, the jig 18 is lowered to dip the partially-sintered element body 15 into the slurry 3 stored in the slurry container 32. After a predetermined time has passed, the jig 18 is lifted upward to get the partially-sintered element body 15 out of the slurry 3.

Then, the partially-sintered element body 15 is completely sintered to obtain the solid electrolytic body 21 whose outer surface 202 is finished into a rough surface as shown in FIG. 1B.

The rest of the second embodiment is substantially identical with that of the first embodiment.

Employing the manufacturing method of the second embodiment makes it possible to form the outer surface of solid electrolytic body 21 into a rough surface whose roughness depends on the grain size and the mixing ratio of the large grains 11 and the small grains 12. The outside electrode 212 is fixed on such a rough surface. The rough surface brings anchor effect which assures an excellent bonding strength. The outside electrode 212 is firmly fixed to the outer surface 202 of solid electrolytic body 21 due to the anchor effect brought by the rough surface. Thus, it becomes possible to obtain the gas sensing element 2 which is capable of effectively preventing the outside electrode 212 from peeling off the solid electrolytic body 21 and is also capable of assuring excellent durability.

Furthermore, according to the second embodiment of the present invention, rotation of rotary vane 36 is once stopped to stabilize the liquid surface level of slurry 3. The dipping treatment for numerous partially-sintered element bodies 15 can be performed at a time in a single slurry tank 31.

As described above, the second embodiment brings an excellent method for manufacturing a gas sensor which assures an excellent bonding force for the outside electrode bonded on the outer surface of the solid electrolytic body.

The performance test for the partially-sintered element body finished with a slurry film in accordance with the second embodiment of the present invention was conducted to check the relationship between the coating density (excluding the binder) and the mixing ratio (weight ratio) of large and small grains contained in the slurry.

Three kinds of slurries, differentiated in the mixing ratio (weight ratio) i.e., 3:7, 4:6 and 5:5, were used in this performance test. The dipping time of the partially-sintered element body in each tested slurry was changed in the range from 7 to 36 seconds.

Figure 8:
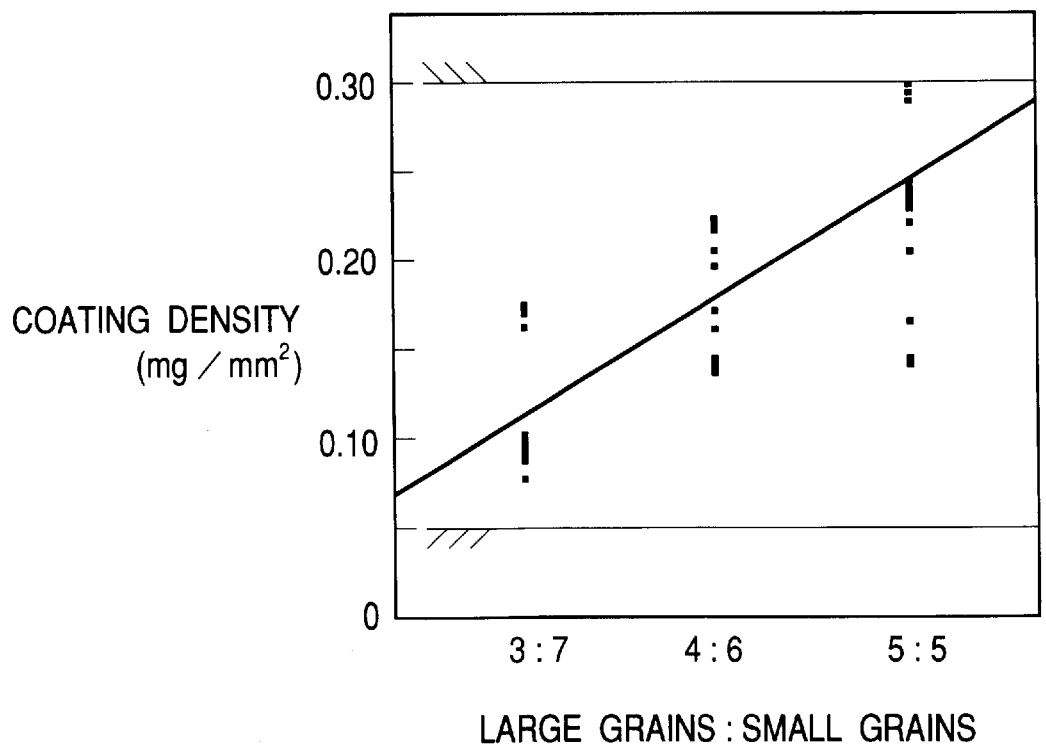
FIG. 8 is a graph showing the relationship between coating density and mixing ratio of large and small grains in accordance with the second embodiment of the present invention.

As the measurement result, FIG. 8 shows the coating density of the slurry film obtained in accordance with the manufacturing method of the second embodiment. The coating density was defined in the following manner.

First, the weight of each tested partially-sintered element body was measured before and after the surface-roughing treatment using the slurry to obtain an increased weight amount of the tested partially-sintered element body. Then, the increased weight amount of the tested partially-sintered element body was divided by an area of the formed slurry film. A weight content of the binder was subtracted from the division value thus obtained to obtain the coating density.

In FIG. 8, the coating density of each slurry is dependent on the dipping time. The coating density is small when the dipping time is short. The coating density is large when the dipping time is long. Thus, the coating density disperses in a relatively wide range depending on the dipping time.

A preferable range of the coating density is 0.05 mg/mm$^2$ to 0.30 mg/mm$^2$.

This measurement has confirmed the fact that the coating density falls into this preferable range when the weight ratio of the large grains to the small grains is set to somewhere from 3:7 to 5:5 and when the dipping time is in an appropriate range from 7 to 36 seconds.

Details of the slurry film having the above-described preferable coating density was later checked through electron microscopic observation.

According to this electron microscopic observation, the large grains protrude from a surface level of the slurry film formed on the outer surface of the partially-sintered element body. And, the large grains are spaced from each other with predetermined clearances or intervals. The following relationship is satisfied, $$0.25d \leq t \leq 0.75d$$

wherein 'd' represents a grain diameter of the large grains and 't' represents a thickness of the slurry film.

This invention may be embodied in several forms without departing from the spirit of essential characteristics thereof. The present embodiments as described are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. A method for manufacturing a gas sensing element which has a cup-shaped solid electrolytic body having a reference gas chamber formed therein, an inside electrode provided on an inner surface of said solid electrolytic body, and an outside electrode provided on an outer surface of the solid electrolytic body, said manufacturing method comprising:

a step of forming a non-sintered element body having a predetermined shape from powdery raw material of said solid electrolytic body;

a step of temporarily sintering said non-sintered element body to obtain a partially-sintered element body as a semi-finished product of said solid electrolytic body;

a step of dipping an outer surface of said partially-sintered element body into a slurry, said slurry containing surface roughing powder including large and small grains which are mutually differentiated in grain size; and a step of completely sintering said partially-sintered element body with a rough slurry film coated thereon into said solid electrolytic body.

2. The manufacturing method for a gas sensing element in accordance with claim 1, wherein a coating density of said slurry during said step of dipping the outer surface of said partially-sintered element body is in a range of 0.05 mg/mm$^2$ to 0.30 mg/mm$^2$ in terms of the amount of said surface roughing powder contained in said slurry.

3. The manufacturing method for a gas sensing element in accordance with claim 1, wherein the grain size of said large grains is in a range from 5 $\mu$m to 50 $\mu$m.

4. The manufacturing method for a gas sensing element in accordance with claim 1, wherein the grain size of said small grains is not larger than 1 $\mu$m.

5. The manufacturing method for a gas sensing element in accordance with claim 4, wherein the grain size of said small grains is in a range from 0.1 $\mu$m to 1 $\mu$m.

6. The manufacturing method for a gas sensing element in accordance with claim 1, wherein the entire content of said large grains is in a range from 5 weight % to 20 weight % when said slurry is 100 weight %.

7. The manufacturing method for a gas sensing element in accordance with claim 1, wherein the entire content of said small grains is in a range from 10 weight % to 20 weight % when said slurry is 100 weight %.

8. The manufacturing method for a gas sensing element in accordance with claim 1, wherein the step of dipping the outer surface of said partially-sintered element body into said slurry containing the surface roughing powder is performed in such a manner that a slurry film is formed on the outer surface of said partially-sintered element body, said large grains protrude from a surface level of said slurry film and are spaced from each other, and the following relationship is satisfied, $$0.25d \leq t \leq 0.75d$$

wherein 'd' represents a grain diameter of said large grains and 't' represents a thickness of said slurry film.

9. The manufacturing method for a gas sensing element in accordance with claim 1, further comprising the following steps for dipping the outer surface of said partially-sintered element body into said slurry containing the surface roughing powder:

a step of preparing a slurry tank equipped with a stirrer therein;

a step of rotating said stirrer to cause rotational flow of said slurry in said slurry tank;

a step of dipping said partially-sintered element body in said slurry in a condition where said stirrer is rotating or stopped; and a step of lifting said partially-sintered element body out of said slurry tank.

10. The manufacturing method for a gas sensing element in accordance with claim 1, further comprising the following steps for dipping the outer surface of said partially-sintered element body into said slurry containing the surface roughing powder:

a step of preparing a slurry tank filled with said slurry;

a step of rotating said partially-sintered element body about its center axis and dipping said partially-sintered element body into said slurry when a stirrer is rotated in said slurry tank, or dipping said partially-sintered element body into said slurry without rotating said partially-sintered element body when said stirrer is not rotated in said slurry tank; and a step of lifting said partially-sintered element body out of said slurry tank.

* * * * *